United States Patent
Nishijima et al.

(10) Patent No.: US 10,101,318 B2
(45) Date of Patent: Oct. 16, 2018

(54) MEASUREMENT APPARATUS

(71) Applicant: FUJIFILM Corporation, Tokyo (JP)

(72) Inventors: Kazuteru Nishijima, Ashigarakami-gun (JP); Tomonori Nishio, Ashigarakami-gun (JP); Toshihito Kimura, Ashigarakami-gun (JP); Toshiaki Kuniyasu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 15/006,581

(22) Filed: Jan. 26, 2016

(65) Prior Publication Data

US 2016/0223516 A1 Aug. 4, 2016

(30) Foreign Application Priority Data

Jan. 30, 2015 (JP) .................................. 2015-016711

(51) Int. Cl.
*G01N 33/49* (2006.01)

(52) U.S. Cl.
CPC .................................. *G01N 33/491* (2013.01)

(58) Field of Classification Search
CPC ... G01N 33/491; G01N 33/2847; G01N 33/18
See application file for complete search history.

(56) References Cited

U.S. PATENT DOCUMENTS

| | | | | |
|---|---|---|---|---|
| 5,946,220 A | * | 8/1999 | Lemelson | B01D 21/302 210/745 |
| 2006/0189926 A1 | | 8/2006 | Hall et al. | |
| 2007/0248492 A1 | * | 10/2007 | Sukawa | B04B 5/0421 422/72 |
| 2010/0221741 A1 | * | 9/2010 | Saiki | G01N 33/491 435/7.1 |
| 2010/0240142 A1 | * | 9/2010 | Saiki | B01L 3/50273 436/164 |

(Continued)

FOREIGN PATENT DOCUMENTS

| | | |
|---|---|---|
| JP | 6-012830 Y2 | 4/1994 |
| JP | 2006-119127 A1 | 5/2006 |
| JP | 2008-529673 A | 8/2008 |

(Continued)

OTHER PUBLICATIONS

Japanese Notification of Reasons for Refusal for corresponding Japanese Application No. 2015-016711, dated Apr. 3, 2018, with Machine translation.

*Primary Examiner* — Manish S Shah
*Assistant Examiner* — Nigel Plumb
(74) *Attorney, Agent, or Firm* — Birch, Stewart, Kolasch & Birch, LLP

(57) ABSTRACT

A centrifugal separation unit that performs centrifugal separation on a sample that has been injected into a container by rotating the container about a center axis of the container, as a rotation axis, a measurement unit that measures a sample component in the container that has been centrifugally separated by the centrifugal separation unit, and a correction unit that performs, on a result of the measurement, correction operation processing based on a change in concentration caused by evaporation of the sample during the centrifugal separation are provided.

11 Claims, 13 Drawing Sheets

(56) References Cited

U.S. PATENT DOCUMENTS

2011/0306856 A1* 12/2011 Rule ................... A61B 5/1427
            600/310
2015/0374900 A1    12/2015 Nishio et al.

FOREIGN PATENT DOCUMENTS

| JP | 2011-501681 A | 1/2011 |
| JP | 2014-208330 A | 11/2014 |
| WO | WO 2006/046537 A1 | 5/2006 |
| WO | WO 2009/049252 A1 | 4/2009 |

* cited by examiner

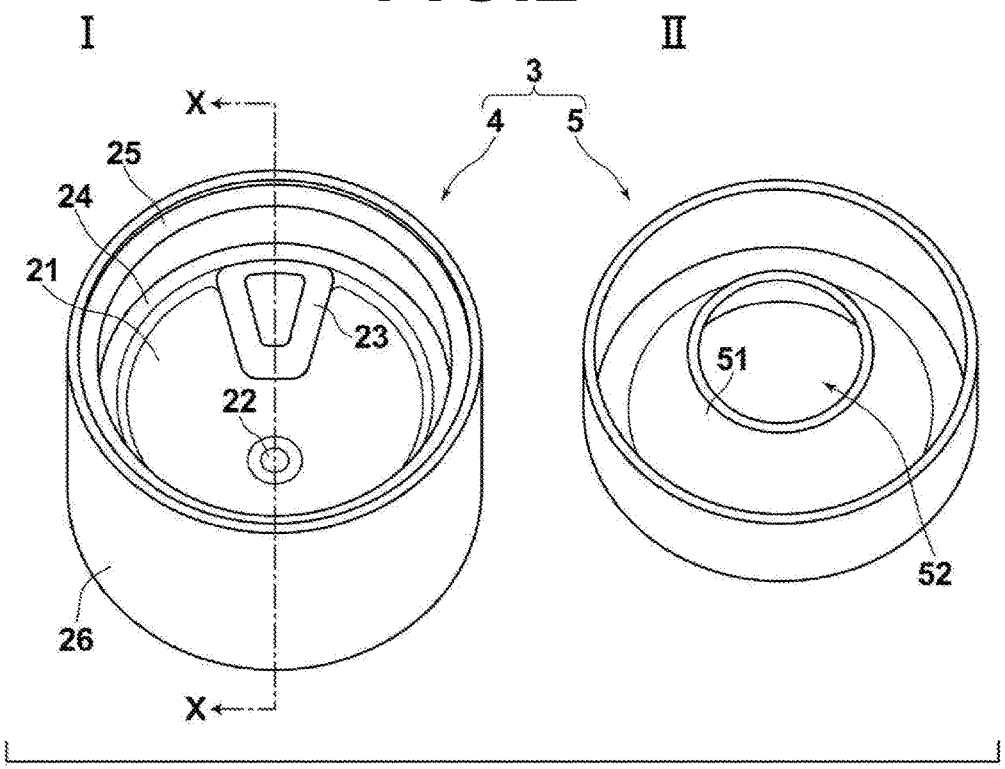
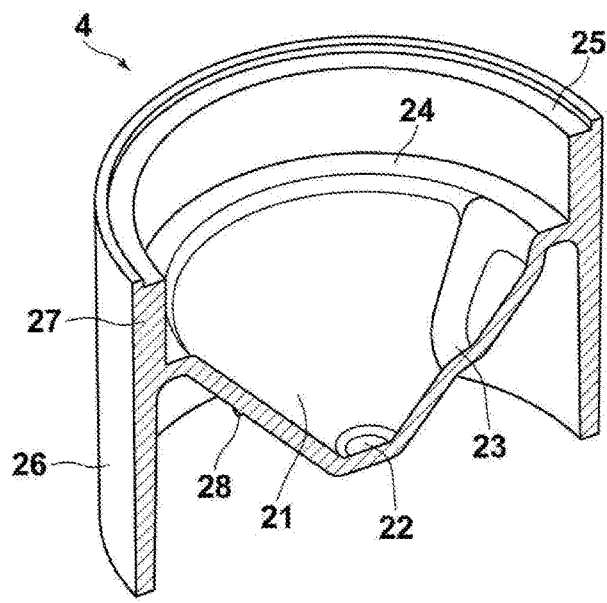

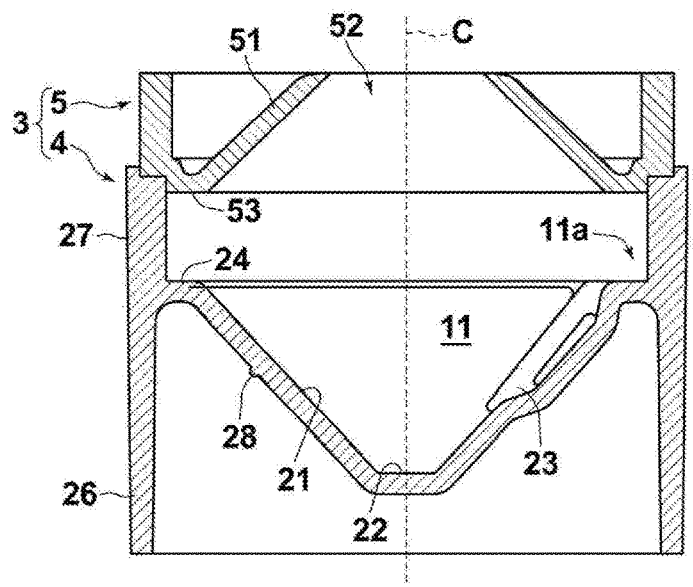
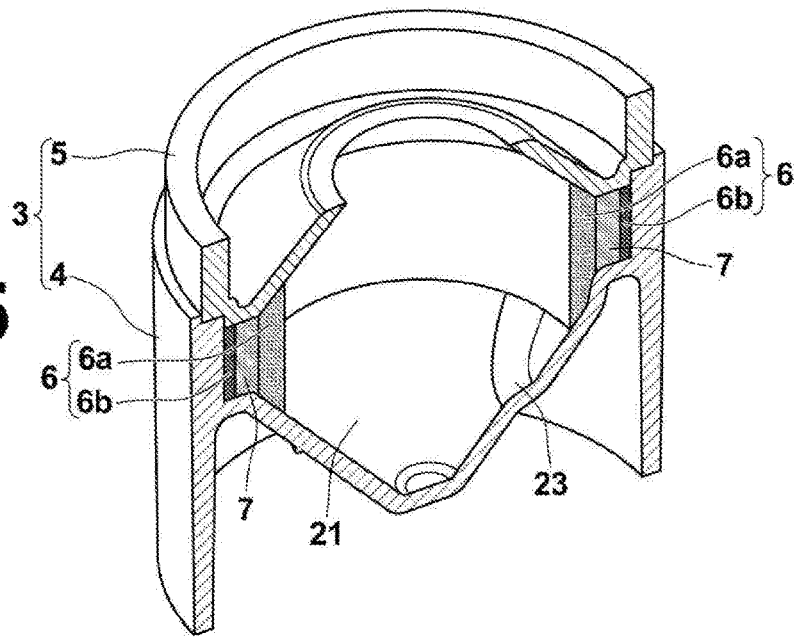

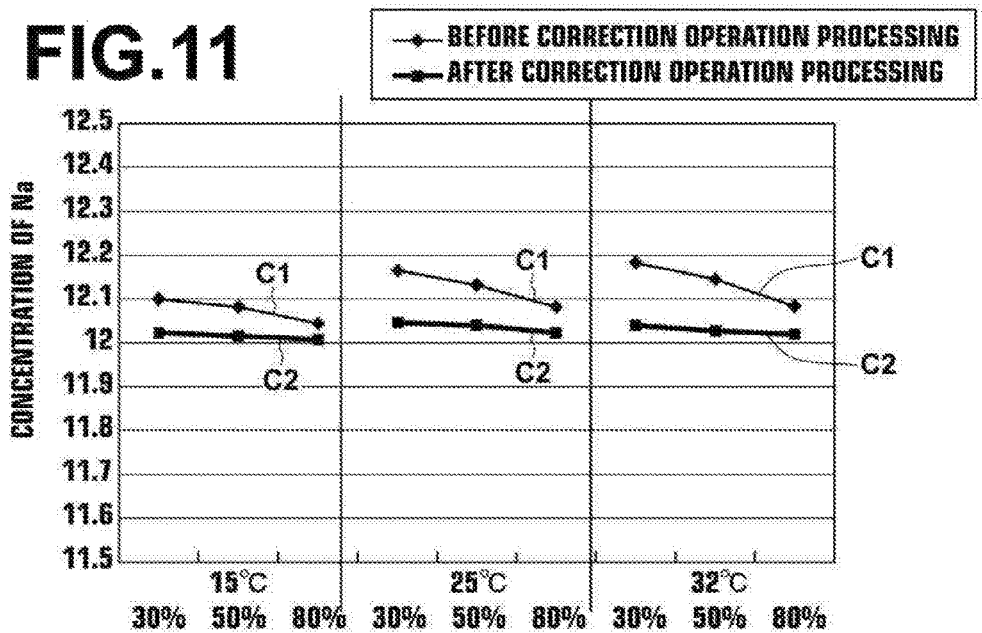
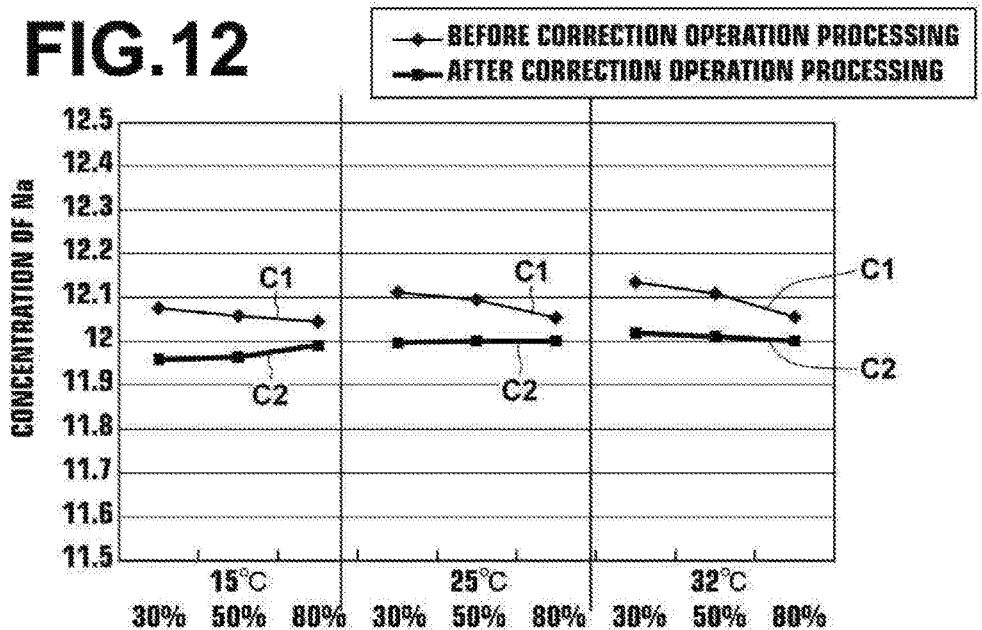

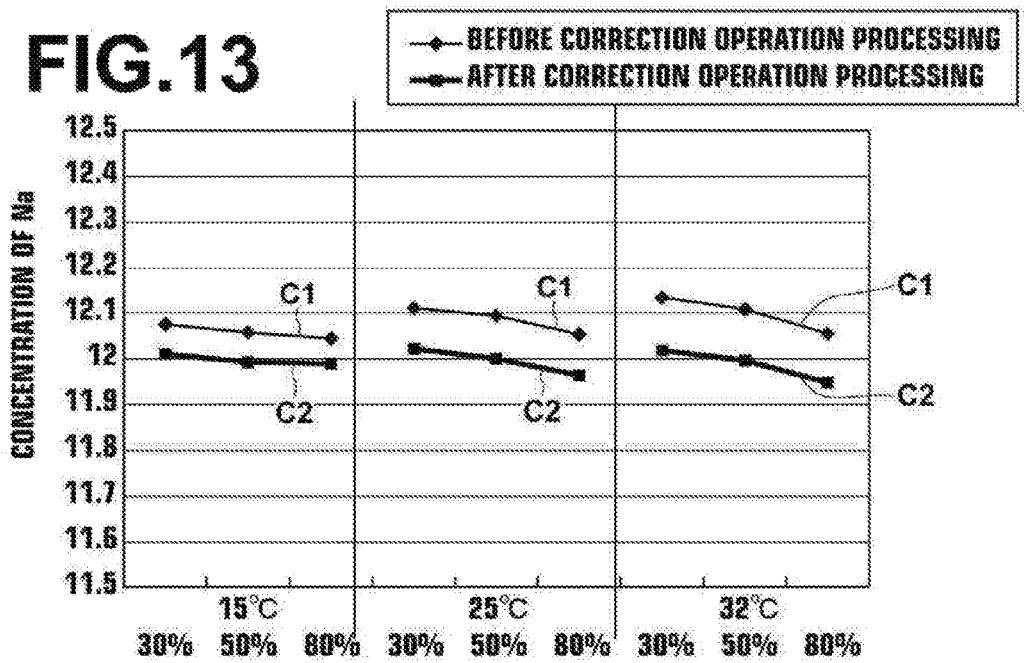
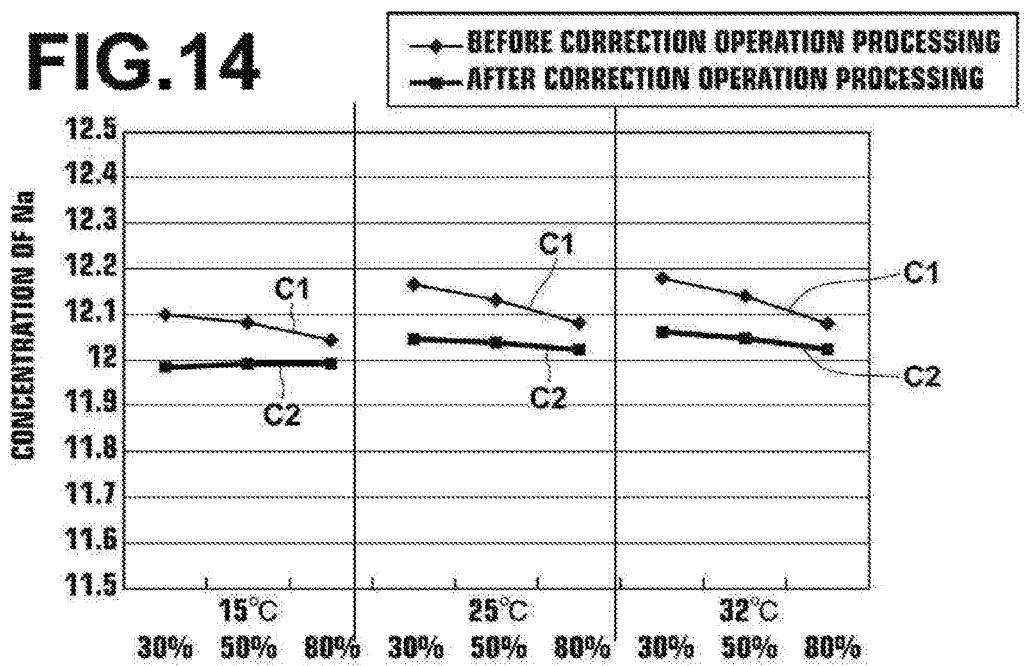

MEASUREMENT APPARATUS

CROSS-REFERENCE TO RELATED APPLICATIONS

The present application claims priority under 35 U.S.C. § 119 to Japanese Patent Application No. 2015-016711, filed on Jan. 30, 2015. The above application is hereby expressly incorporated by reference, in its entirety, into the present application.

BACKGROUND

The present disclosure relates to a measurement apparatus that measures a sample component that has been centrifugally separated by rotation-type centrifugal separation.

Conventionally, centrifugal separation apparatuses, which centrifugally separate each component of a sample such as blood in a container, were known. As such centrifugal separation apparatuses, there are so-called revolution-type centrifugal separation apparatuses and so-called rotation-type centrifugal separation apparatuses.

FIG. 19 is a schematic diagram illustrating the configuration of a revolution-type centrifugal separation apparatus and its operation. As illustrated in FIG. 19, a revolution-type centrifugal separation apparatus performs centrifugal separation by revolving blood collection tube P1, in which blood BL and separation agent S are stored, or the like with a sealing closure set thereon. Specifically, each component of blood BL in blood collection tube P1 is centrifugally separated by rotating rotation shaft Q1 on which blood collection tube P1 has been set by motor M1. Accordingly, extraction of blood plasma component BP alone is possible.

Meanwhile, FIG. 20 is a schematic diagram illustrating the configuration of a rotation-type centrifugal separation apparatus and its operation. As illustrated in FIG. 20, a rotation-type centrifugal separation apparatus uses container P2 for centrifugal separation including an inclined inner wall that becomes higher from the center toward the outer circumference, and in which a retention part that retains a sample in the inside of the container is formed. Specifically, after blood BL is stored in the retention part in container P2 for centrifugal separation, container P2 for centrifugal separation itself is rotated by rotation of rotation shaft Q2 by motor M2. Centrifugal force induced by such rotation of container P2 for centrifugal separation separates each component of blood BL in such a manner that deposits are formed, in order from a component having lowest specific gravity, from the inner circumference toward the outer circumference. Then, when the rotation of the container for centrifugal separation is stopped, generally, a component having low specific gravity (blood plasma component BP) closer to the inner circumference exfoliates from the deposits, and is retained at a bottom of the container for centrifugal separation.

In the revolution-type centrifugal separation apparatus, a distance of movement of blood cells is generally long. Therefore, a relatively long time is required to separate a blood plasma component and blood cells from each other. In contrast, in the rotation-type centrifugal separation apparatus, a distance of movement of blood cells is short. Therefore, it is possible to shorten the length of time for centrifugal separation. Further, the rotation-type centrifugal separation apparatus has a merit that reduction in the size of the apparatus is possible, compared with the revolution-type centrifugal separation apparatus.

SUMMARY

However, an opening for inserting a nozzle for injecting blood or taking out a blood plasma component is provided on a top surface of the container for centrifugal separation used in the rotation-type centrifugal separation apparatus, and flow F of air is generated at this opening during centrifugal separation. A change of air at a gas-liquid interface is fast because of this flow F of air, and the area of a surface of blood in contact with air is large. Therefore, evaporation of the blood plasma component during centrifugal separation progresses fast, compared with natural evaporation. Especially, when the amount of the blood plasma component is small, the area of the surface of the blood plasma component in contact with air is large relative to the volume of the blood plasma component. Therefore, a change in concentration by evaporation tends to be large. In other words, when the blood plasma component is centrifugally separated by using the rotation-type centrifugal separation apparatus, it is difficult to accurately measure the concentration of a biochemical substance in the blood plasma component.

To solve such problems, for example, a sealing closure may be provided at an opening of the container for centrifugal separation also in the rotation-type centrifugal separation apparatus. However, that is not a very realistic solution because a configuration for removing the sealing closure is required to automatically perform all the process from centrifugal separation to measurement. However, if no sealing closure is provided, the concentration of Na (sodium) or the like in blood becomes higher by evaporation of water in the blood plasma as described above. Further, gas, such as $CO_2$ (carbon dioxide), dissolved in the blood plasma evaporates. Therefore, it is impossible to accurately measure the concentration of Na and the concentration of $TCO_2$ (total carbon dioxide). Hence, a measurement result is different from a result of measuring a component in the blood plasma that has been centrifugally separated by a revolution-type centrifugal separation apparatus, which is different from the rotation-type centrifugal separation apparatus.

Japanese Unexamined Patent Publication No. 2006-119127 (Patent Document 1), Pamphlet of International Publication No. 2006-046537 (Patent Document 2) and Japanese Utility Model Publication No. 6 (1994)-012830 (Patent Document 3) disclose providing an additional configuration for suppressing evaporation of a sample, as described above. However, if an additional configuration is provided, the cost increases.

In view of the foregoing circumstances, the present disclosure provides a measurement apparatus that can obtain a more accurate result of measuring a sample component that has been centrifugally separated by a rotation-type centrifugal separation apparatus.

A measurement apparatus of the present disclosure includes a centrifugal separation unit that performs centrifugal separation on a sample that has been injected into a container by rotating the container about a center axis of the container, as a rotation axis, a measurement unit that measures a sample component in the container that has been centrifugally separated by the centrifugal separation unit, and a correction unit that performs, on a result of the measurement, correction operation processing based on a change in concentration caused by evaporation of the sample during the centrifugal separation.

In the measurement apparatus of the present disclosure, the measurement unit may measure also a sample component that has been centrifugally separated by an external centrifugal separation unit other than the centrifugal separation unit. The correction unit does not perform the correction operation processing on a result of the measurement of the sample component that has been centrifugally separated by the external centrifugal separation unit. Alternatively, the correction unit may perform correction operation processing on the result of the measurement of the sample component that has been centrifugally separated by the external centrifugal separation unit by using an operation parameter different from an operation parameter that was used when the correction operation processing was performed on the result of measurement of the sample component that had been centrifugally separated by the centrifugal separation unit.

Further, the apparatus may include an atmospheric pressure information obtainment unit that obtains atmospheric pressure information, and the correction unit may perform, based on the atmospheric pressure information, the correction operation processing on the result or results of measurement.

Further, the apparatus may include a temperature information obtainment unit that obtains ambient temperature information, and the correction unit may perform, based on the ambient temperature information, the correction operation processing on the result or results of measurement.

Further, the apparatus may include a humidity information obtainment unit that obtains ambient humidity information, and the correction unit may perform, based on the ambient humidity information, the correction operation processing on the result or results of measurement.

Further, the apparatus may include a time information obtainment unit that obtains information about the length of time of the centrifugal separation, and the correction unit may perform, based on the information about the length of time of the centrifugal separation, the correction operation processing on the result or results of measurement.

Further, the apparatus may include a sample amount information obtainment unit that obtains information about the amount of the sample component that has been centrifugally separated, and the correction unit may perform, based on the information about the amount of the sample component, the correction operation processing on the result or results of measurement.

Further, when the sample is blood, the sample amount information obtainment unit may obtain information about a hematocrit value of the blood, and obtain, based on the information about the hematocrit value, information about the amount of a blood plasma component, as the information about the amount of the sample component.

Further, the apparatus may include an information obtainment unit that obtains atmospheric pressure information, ambient temperature information, ambient humidity information, information about the length of time of the centrifugal separation, and information about the amount of the sample component. The correction unit may perform, based on the atmospheric pressure information, the ambient temperature information, the ambient humidity information, the information about the length of time of the centrifugal separation, and the information about the amount of the sample component, correction operation processing on the result of the measurement.

Further, the measurement unit may measure a gas component included in the sample on which the centrifugal separation has been performed, and the correction unit may perform, based on the amount of the gas component evaporated by the centrifugal separation, the correction operation processing on the result or results of measurement.

Further, the apparatus may include a container information obtainment unit that obtains information about a container into which the sample to be measured has been injected, and the correction unit may perform, based on the information about the container, the correction operation processing on the result of measurement.

Further, the correction unit may store operation parameters that correspond to information about plural containers.

According to the measurement apparatus of the present disclosure, correction operation processing based on a change in concentration caused by evaporation of a sample during centrifugal separation is performed on a sample component separated by rotation-type centrifugal separation. Therefore, a more accurate measurement result is obtainable. Further, it is possible to obtain a measurement result similar to a result of measuring a sample component separated by revolution-type centrifugal separation.

BRIEF DESCRIPTION OF THE DRAWINGS

FIG. 2 is a schematic diagram illustrating the structure of a container for centrifugal separation;

FIG. 3 is a schematic perspective view of X-X cross section of a container main body 4;

FIG. 4 is a schematic sectional view illustrating an internal structure of the container main body 4 at X-X cross section;

FIG. 5 is a schematic sectional view illustrating a state of the inside of the container for centrifugal separation during centrifugal separation;

FIG. 11 is a chart showing concentration C2 after correction operation processing when an atmospheric pressure and the amount of a blood plasma component are fixed values;

FIG. 12 is a chart showing concentration C2 after correction operation processing when an ambient temperature and an atmospheric pressure are fixed values;

FIG. 13 is a chart showing concentration C2 after correction operation processing when an ambient humidity and an atmospheric pressure are fixed values;

FIG. 14 is a chart showing concentration C2 after correction operation processing when the amount of a blood plasma component, an ambient temperature and an atmospheric pressure are fixed values;

DETAILED DESCRIPTION OF THE PREFERRED EMBODIMENTS

Figure 1:
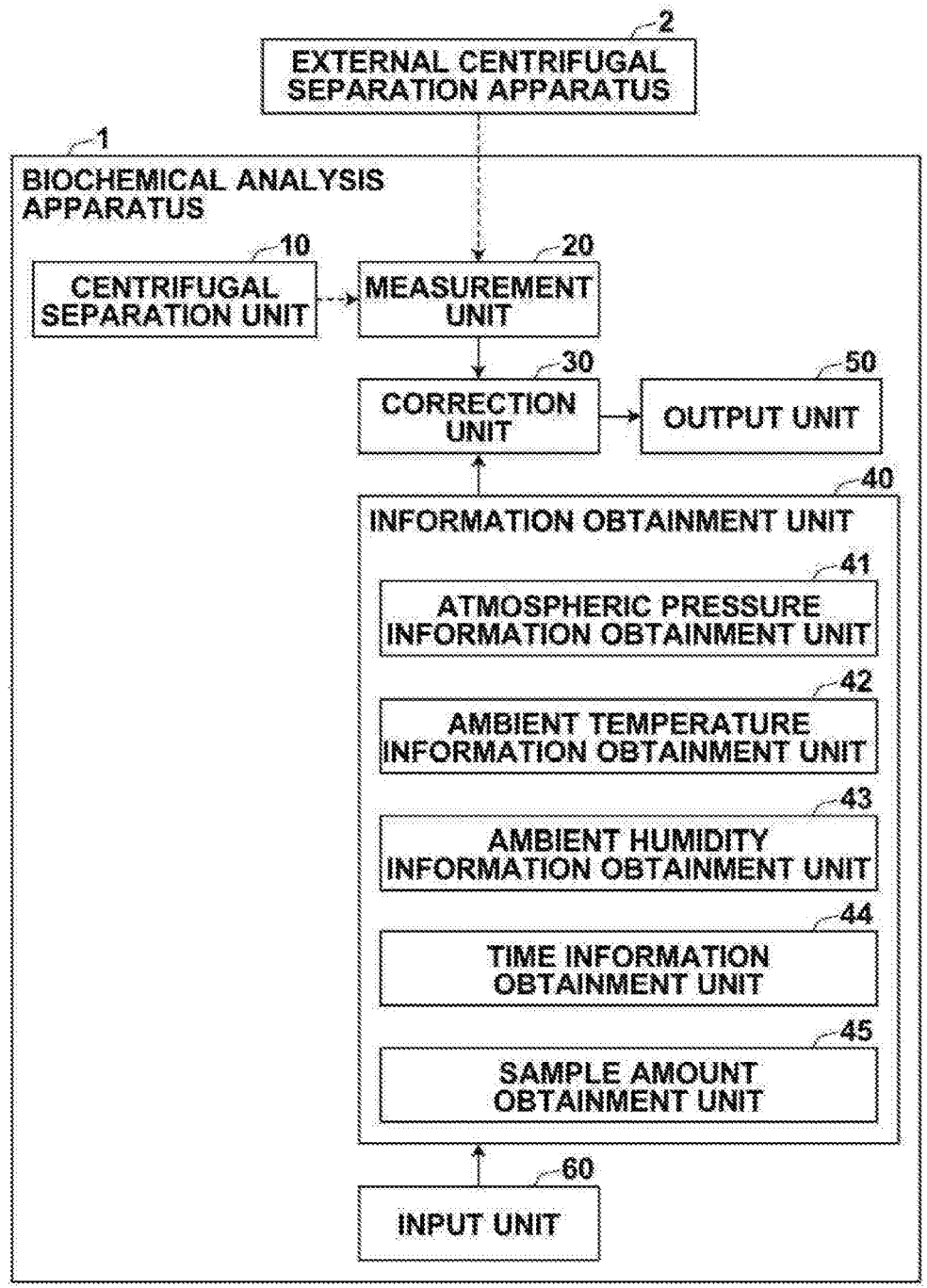
FIG. 1 is a schematic block diagram illustrating the configuration of a biochemical analysis apparatus using an embodiment of a measurement apparatus of the present disclosure.

Hereinafter, a biochemical analysis apparatus using an embodiment of a measurement apparatus of the present disclosure will be described in detail in reference with drawings. FIG. 1 is a schematic block diagram illustrating the configuration of a biochemical analysis apparatus according to an embodiment of the present disclosure.

A biochemical analysis apparatus 1 according to an embodiment of the present disclosure includes a centrifugal separation unit 10, a measurement unit 20, a correction unit 30, an information obtainment unit 40, an output unit 50, and an input unit 60, as illustrated in FIG. 1.

The centrifugal separation unit 10 performs centrifugal separation on a sample injected into a container for centrifugal separation, which will be described later, by rotating the container for centrifugal separation about a center axis of the container for centrifugal separation, as a rotation axis.

The measurement unit 20 measures a sample component that has been centrifugally separated by the centrifugal separation unit 10. Further, the measurement unit 20 is able to measure not only a sample component that has been centrifugally separated by the centrifugal separation unit 10 provided in the biochemical analysis apparatus 1 but also a sample component that has been centrifugally separated by an external centrifugal separation apparatus 2, which is different from the biochemical analysis apparatus 1.

The correction unit 30 performs correction operation processing on a result of measurement by the measurement unit 20. This correction operation processing is performed to correct a change in concentration caused by evaporation of a sample during centrifugal separation by the centrifugal separation unit 10. More specifically, the correction unit 30 of the present embodiment performs, based on information related to evaporation of the sample obtained by the information obtainment unit 40, correction operation processing on the measurement result.

Further, the correction unit 30 performs the aforementioned correction operation processing on the result of measurement of the sample component that has been centrifugally separated by the centrifugal separation unit 10, but does not perform the correction operation processing on the result of measurement of the sample component that has been centrifugally separated by the external centrifugal separation apparatus 2. Alternatively, the correction unit 30 may perform correction operation processing on the result of measurement of the sample component that has been centrifugally separated by the external centrifugal separation apparatus 2 by using an operation parameter different from an operation parameter that was used when correction operation processing was performed on the result of measuring the sample component that has been centrifugally separated by the centrifugal separation unit 10. Correction operation processing at the correction unit 30 will be described later in detail.

The information obtainment unit 40 includes an atmospheric pressure information obtainment unit 41 that obtains atmospheric pressure information, an ambient temperature information obtainment unit 42 that obtains ambient temperature information, an ambient humidity information obtainment unit 43 that obtains ambient humidity information, a time information obtainment unit 44 that obtains information about the length of time of centrifugal separation at the centrifugal separation unit 10, and a sample amount information obtainment 45 that obtains information about the amount of a sample component that has been centrifugally separated.

The atmospheric pressure information obtainment unit 41, the ambient temperature information obtainment unit 42, and the ambient humidity information obtainment unit 43 obtain information detected by an atmospheric pressure sensor, a temperature sensor and a humidity sensor, respectively. Each of the sensors will be described later in detail. Further, each of the information about the length of time of centrifugal separation to be obtained by the time information obtainment unit 44 and the information about the amount of the sample component to be obtained by the sample amount information obtainment 45 is set by an input by a user using the input unit 60 including a keyboard, a touch panel or the like. Here, at least one of the atmospheric pressure information, the ambient temperature information and the ambient humidity information may also be set by an input by the user. It is not always necessary that the user directly sets the atmospheric pressure information by an input. For example, since atmospheric pressure is determined by a place where the biochemical analysis apparatus 1 is installed, the user may set information about the installation place by an input. In this case, a correspondence table between installation places and atmospheric pressure information may be stored in advance in the atmospheric pressure information obtainment unit 41, and the atmospheric pressure information may be obtained from this table.

Further, the information about the length of time of centrifugal separation to be obtained by the time information obtainment unit 44 may be automatically measured. Specifically, for example, the transmittance of light through a sample component (blood plasma component) during centrifugal separation may be measured, and time when this transmittance of light has become less than or equal to a predetermined threshold may be obtained. Further, the length of time from the start of centrifugal separation till the obtained time may be obtained as the length of time of centrifugal separation.

The output unit 50 outputs an operation result on which correction operation processing has been performed at the correction unit 30. Specifically, the output unit 50 includes a display device, such as a liquid crystal display, and displays the operation result on the display device. Here, the output unit 50 may output the operation result to a data server apparatus or the like to be stored instead of only displaying the operation result on the display device. Further, the output unit 50 may output the operation result to a printing device or the like, and output the operation result on a printed sheet.

Next, an embodiment of a container for centrifugal separation set in the centrifugal separation unit 10 will be described.

FIG. 2 is a schematic diagram illustrating the structure of a container 3 for centrifugal separation according to an embodiment of the present disclosure. Section I in FIG. 2 is a perspective view of a container main body 4 of the container 3 for centrifugal separation, and section II in FIG. 2 is a perspective view of a lid unit 5 of the container 3 for centrifugal separation. Further, FIG. 3 is a schematic perspective view of the container main body 4 at X-X cross section illustrated in section I in FIG. 2. FIG. 4 is a schematic sectional view illustrating an internal structure of the container main body 4 at X-X cross section.

As illustrated in FIG. 2 through FIG. 4, the container 3 for centrifugal separation of the present embodiment includes the container main body 4 and the lid unit 5. The container main body 4 includes an inclined inner wall part 21, a bottom part 22, a trap bottom surface part 24, a trap side surface part 27, a fitting part 25, which is to be fitted with the lid unit 5, and a support outer wall part 26, which supports these parts.

The lid unit 5 includes an opening part 51, in which an opening 52 for injecting a sample is formed, and a trap upper surface part 53, which forms a trap space 11a together with the trap bottom surface part 24 and the trap side surface part 27 when the lid unit 5 is fitted with the container main body 4.

The container 3 for centrifugal separation has an internal structure that is symmetric with respect to an axis (center axis C of the container for centrifugal separation) that passes through a center of the bottom part 22 and is perpendicular to the bottom part 22 (in other words, a structure similar to a kind of rotation body about center axis C as a center). Further, the container 3 for centrifugal separation has a cylindrical shape when viewed from the outside. When centrifugal separation is performed, the lid unit 5 in a state of being fitted with the fitting part 25 of the container main body 4 is, for example, firmly fixed to the fitting part 25, and the container 3 for centrifugal separation is rotated about center axis C, as a rotation axis.

As illustrated in FIG. 4, a retention space 11, into which a sample is injected, is formed by fitting the container main body 4 and the lid unit 5 together. Specifically, this retention space 11 is a space surrounded by the inclined inner wall part 21, the bottom part 22, the trap bottom surface part 24, the trap side surface part 27, the trap upper surface part 53 and the opening part 51. In this retention space, especially the space 11a, formed by the trap bottom surface part 24, the trap side surface part 27 and the trap upper surface part 53, is a trap space in which a component having high specific gravity is trapped when centrifugal separation has been performed on a sample by rotating the container 3 for centrifugal separation.

The inclined inner wall part 21 is a funnel-shaped inclined surface, and formed in such a manner that the diameter of a cross section of the opening of the retention space 11 is tapered from its opening edge. Further, a depression portion 23 is formed on the inclined inner wall part 21. Further, a projection portion 28 is formed on the inclined inner wall part 21 in such a manner that the position of the projection portion 28 and the position of the depression portion 23 are symmetric with respect to center axis C.

The projection portion 28 is provided to adjust the position of the center of gravity of the container 3 for centrifugal separation. The projection portion 28 has been formed because the depression portion 23 was formed on the inclined inner wall part 21. Here, if a shift in the position of the center of gravity is not large (if the noise and vibration of the apparatus is not a problem, or the like), it is not always necessary to form the projection portion 28.

The trap space 11a has a ring shape with center axis C, as its center, and the volume of the trap space 11a is designed based on the amount of a sample to be injected. Further, for example, a separation agent (or separation gel) is placed in advance in the trap space 11a. This separation agent is appropriately selected, based on a component having low specific gravity and a component having high specific gravity to be separated from each other in a sample, from materials having specific gravity in the middle of the specific gravity of the component having low specific gravity and the specific gravity of the component having high specific gravity. Specifically, when blood plasma (a component having low specific gravity) and blood cells (a component having high specific gravity) in blood are separated from each other, a material having specific gravity in the middle of the specific gravity of blood plasma and the specific gravity of blood cells should be selected.

The opening part 51 of the lid unit 5 has, for example, a truncated conical shape. The opening part 51 has an inclined surface formed in such a manner that the diameter of a cross section of the opening is tapered toward the opening 52. An upper part of the retention space 11 is formed by this inclined surface.

Next, the function of the aforementioned container 3 for centrifugal separation will be described. Centrifugal separation is performed by rotating the aforementioned container 3 for centrifugal separation with respect to center axis C, as a rotation axis. FIG. 5 is a schematic sectional view illustrating the state of the inside of the container for centrifugal separation during centrifugal separation. FIG. 5 illustrates a state in which deposits, as a resultant of centrifugal separation, have been formed in a region closer to the outer circumference of retention space 11 by performing centrifugal separation on a sample 6 including a component 6a having low specific gravity and a component 6b having high specific gravity. These deposits are a layer of the component 6a having low specific gravity, a layer of separation agent 7, and a layer of the component 6b having high specific gravity deposited in this order from the inner circumference side.

As illustrated in FIG. 5, the depression portion 23 is provided at an outer circumference edge portion of the inclined inner wall part 21. Consequently, a part of the component 6a having low specific gravity that is present on the depression portion 23 exfoliates from the deposits more easily, compared with a part of the component 6a that is present in the other area.

Figure 6:
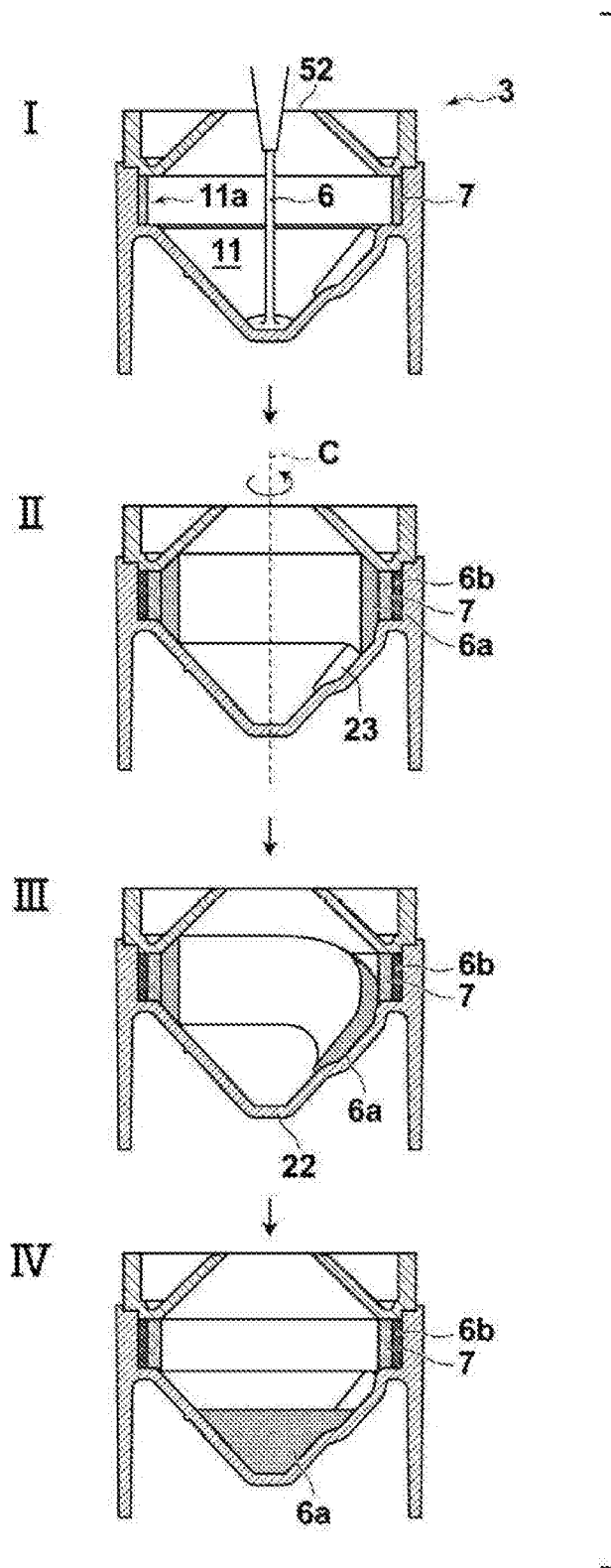
FIG. 6 is a diagram illustrating steps of centrifugal separation.

Next, the process of centrifugal separation using the aforementioned container 3 for centrifugal separation will be described. FIG. 6 is a diagram illustrating the process of centrifugal separation.

First, the container 3 for centrifugal separation in which a separation agent 7 has been placed in advance in the trap space 11a is prepared. A sample 6 is injected into the retention space 11 from the opening 52 of the container 3 for centrifugal separation (section I of FIG. 6). Next, the container 3 for centrifugal separation into which the sample 6 has been injected is set in the centrifugal separation unit 10, and rotated. At this time, the contents of the container 3 for centrifugal separation are separated according to specific gravity by centrifugal force of rotation, and deposits are formed closer to the outer circumference of the retention space 11 (section II of FIG. 6). A component 6b having high specific gravity is trapped in the trap space 11a by the separation agent 7.

Then, when rotation of the container 3 for centrifugal separation stops, exfoliation of a part of the component 6a having low specific gravity that is present on the depression portion 23 starts (section III of FIG. 6). Further, exfoliation of the other part of the component 6a having low specific gravity gradually progresses in such a manner to follow the exfoliation of the part of the component 6a having low specific gravity on the depression portion 23. Meanwhile, the component 6a having high specific gravity remains, as it is, in the trap space 11a. Then, when all the component 6a having low specific gravity exfoliates from the deposits, the component 6a having low specific gravity accumulates in a lower part of the retention space 11, and a state in which the component 6a having low specific gravity alone has been extracted and become collectable is induced (section IV of FIG. 6).

Figure 7:
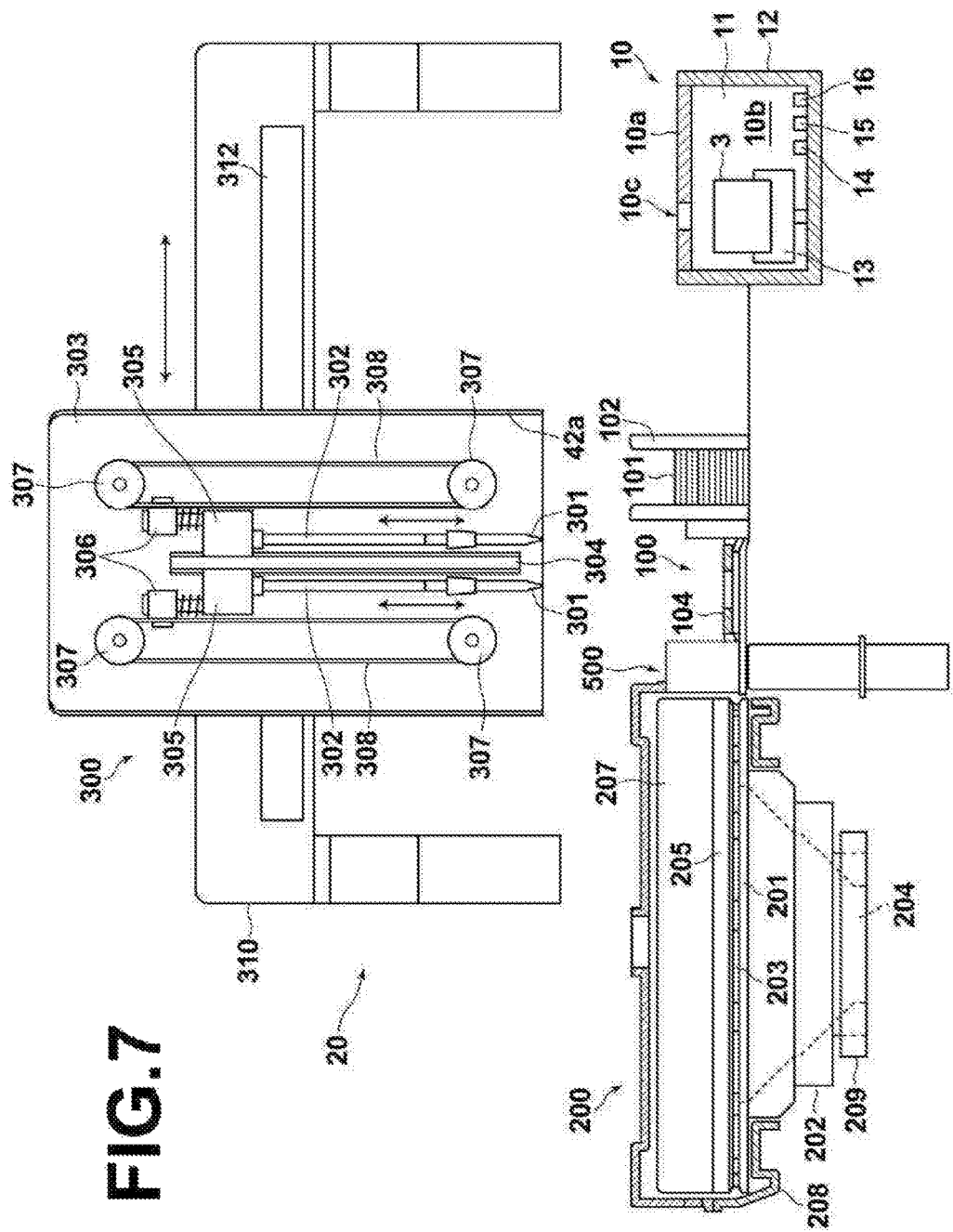
FIG. 7 is a schematic frontal sectional view illustrating the configuration of a centrifugal separation unit and a measurement unit.
Figure 8:
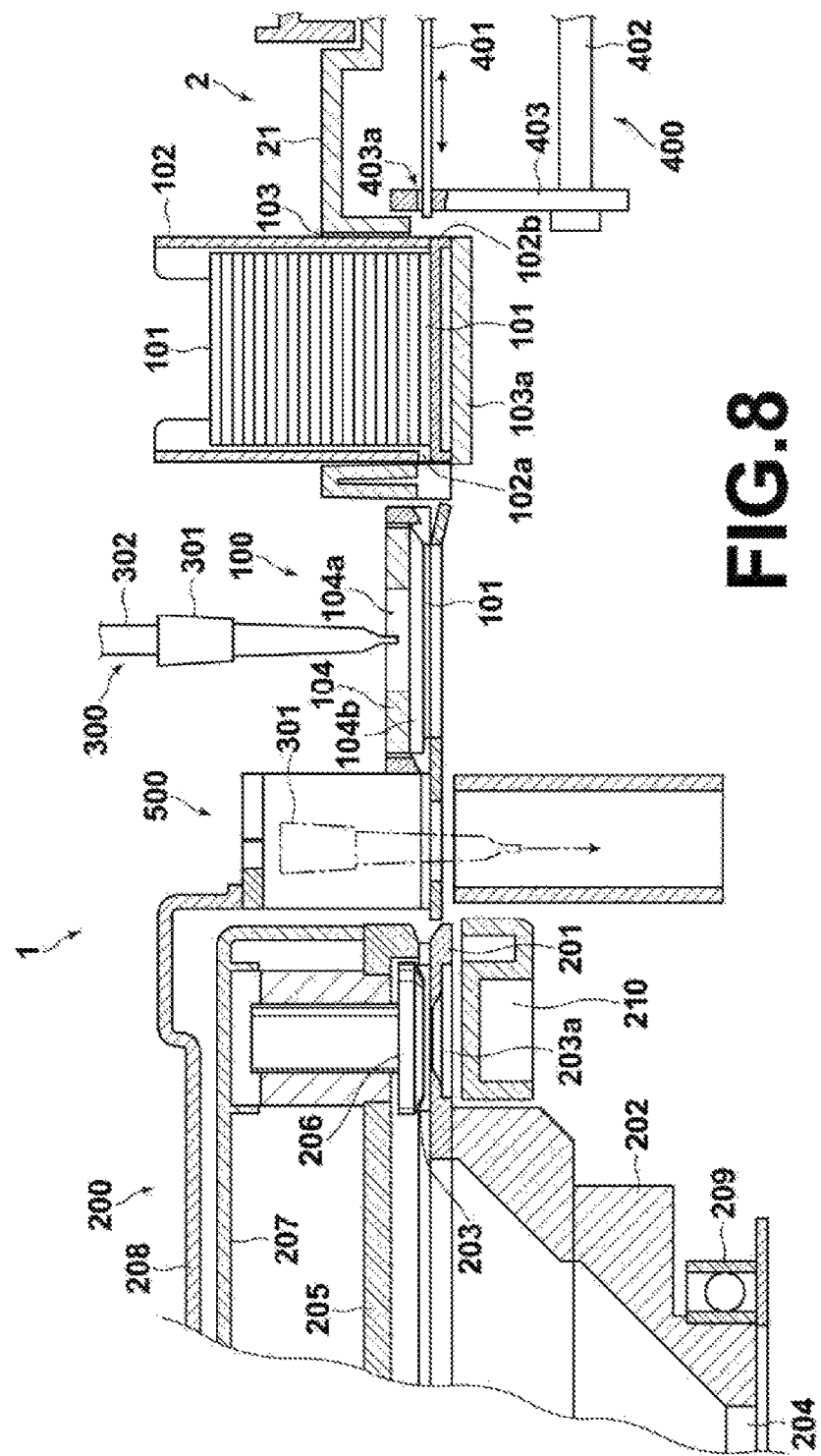
FIG. 8 is an enlarged sectional view of the vicinity of a spot application unit.

Next, the configuration of the centrifugal separation unit 10 and the measurement unit 20 of the biochemical analysis apparatus 1 of the present embodiment will be described in detail with reference to FIG. 7 and FIG. 8. FIG. 7 is a schematic frontal sectional view illustrating the configuration of the centrifugal separation unit 10 and the measurement unit 20. FIG. 8 is an enlarged sectional view of the vicinity of a spot application unit in the measurement unit 20 illustrated in FIG. 7.

As illustrated in FIG. 7 and FIG. 8, the measurement unit 20 includes a spot application unit 100, an incubator 200, a light measurement head 210, a spot application mechanism 300, an element conveyance mechanism 400 (not illustrated in FIG. 7), a chip discarding unit 500, a control unit that controls various mechanisms, and the like.

The spot application unit 100 is a part in which a spot of sample component, such as blood plasma, that has been centrifugally separated is applied to a dry analysis element 101 that has been conveyed. In the present embodiment, a dry analysis element 101 of colorimetric measurement type is conveyed to the spot application unit 100, and a spot of sample component is applied to the dry analysis element 101 by the spot application mechanism 300.

As illustrated in FIG. 8, the spot application unit 100 includes an element holding part 104 in which an opening 104a for spot application is formed. Further, a space 104b through which the dry analysis element 101 passes is formed under the element holding part 104.

The dry analysis element 101 is arranged in the space 104b by the element conveyance mechanism 400. After spot application is performed on the dry analysis element 101 by the spot application mechanism 300, the dry analysis element 101 is pushed out by the element conveyance mechanism 400, and transferred to the incubator 200.

As illustrated in FIG. 8, the element conveyance mechanism 400 includes an element conveyance member 401 that conveys the dry analysis element 101 from an element cartridge 102, which will be described later, to the spot application unit 100, and further to the incubator 200. The element conveyance member 401 is slidably supported by a guide rod 402, and operated by a drive mechanism, which is not illustrated, to move forward and backward. A leading end of the element conveyance member 401 is inserted to a guide hole 403a of a vertical plate 403, and slides through this guide hole 403a.

Further, the chip discarding unit 500 at which the nozzle chip 301 is discarded is arranged after the spot application unit 100.

The incubator 200 has a circular shape. The incubator 200 stores and keeps the dry analysis element 101 of colorimetric type at a constant temperature for a predetermined time, and performs colorimetric measurement.

The spot application mechanism 300 is arranged at an upper position, and a spot application nozzle 302 that is upwardly and downwardly movable applies a spot of sample component. A nozzle chip 301 is attached to a leading end of the spot application nozzle 302, and the spot application nozzle 302 discharges the sample component into the nozzle chip 301. The nozzle chip 301 after use is removed at the chip discarding unit 500, and dropped down, and discarded.

The spot application mechanism 300 includes a movement frame 303 that is held on a horizontal guide rail 312 of a fixed frame 310 in such a manner that the movement frame 303 is horizontally movable. Further, two spot application nozzles 302 are set in this movement frame 303 in such a manner that the spot application nozzles 302 are vertically movable. A vertical guide rail 304 is provided at a center of the movement frame 303, and two nozzle fixing bases 305 are slidably held on either side of this vertical guide rail 304. Upper ends of the spot application nozzles 302 are firmly fixed to lower parts of the nozzle fixing bases 305, respectively. Further, shaft-shaped members that extend upward are provided on upper sides of the nozzle fixing bases 305, and inserted through drive transmission members 306. The fitting force of the nozzle chips 301 is obtainable by compression springs interposed between the nozzle fixing bases 305 and the drive transmission members 306. The nozzle fixing base 305 is vertically movable together with the drive transmission member 306. Further, when the nozzle chip 301 is fitted on the leading end of the spot application nozzle 302, the drive transmission member 306 is downwardly movable against the nozzle fixing base 305 by compression of the compression spring. The drive transmission member 306 is fixed to a belt 308 set around upper and lower pulleys 307, and vertically movable based on the movement of the belt 308 run by a motor, which is not illustrated.

Further, the movement frame 303 is driven in a horizontal direction by a belt drive mechanism, which is not illustrated. The horizontal movement and the vertical movement of the two nozzle fixing bases 305 are controlled in such a manner that the two nozzle fixing bases 305 vertically move independently from each other. Further, the two spot application nozzles 302 are structured in such a manner that they horizontally move together, and that they vertically move independently from each other.

The spot application nozzle 302 is formed in a rod shape, and an air passage channel is provided in the spot application nozzle 302. A pipette-shaped nozzle chip 301 is fitted, in a sealed state, onto the lower end of the spot application nozzle 302.

Further, the element cartridge 102 is provided in the vicinity of the spot application unit 100. As illustrated in FIG. 8, plural dry analysis elements 101 before use are piled and inserted to the element cartridge 102 from an upper direction. When the element cartridge 102 is mounted on an element mounting unit 103, a lower end of the element cartridge 102 is held on a bottom wall 103a of the element mounting unit 103. A dry analysis element 101 at a lowest portion of the element cartridge 102 is located at the same height as an element conveyance plane. An opening through which only one dry analysis element 101 is passable is formed on a side of the lowest portion facing the spot application unit 100. On the opposite side of the lowest portion, an opening 102b through which an element conveyance member 401 is insertable is formed.

The incubator 200 that performs colorimetric measurement includes a ring-shaped rotation member 201 at an outer circumference portion. The rotation member 201 is rotationally supported by a lower bearing 209 via a rotation barrel 202. Plural depression portions are formed at predetermined intervals on the circumference of a circle on the upper surface of the rotation member 201. Element chambers 203 composed of slit-shaped spaces are formed by these depression portions (please refer to FIG. 8).

Further, an inner hole of the rotation barrel 202 is formed as a hole 204 for discarding a dry analysis element 101 after measurement. The dry analysis element 101 in the element chamber 203 is directly moved toward the center of the rotation barrel 202, and dropped down, and discarded.

A member 205 in which a heating means is arranged is provided in an upper direction of the rotation member 201. It is possible to keep the dry analysis element 101 at a predetermined constant temperature in the element chamber 203 by adjustment of the temperature by the heating means. Further, a holding member 206 that prevents evaporation of a sample component by holding the dry analysis element 101 from an upper side is arranged at a position in the member 205 corresponding to the element chamber 20. A thermal insulation cover 207 is arranged in an upper direction of the member 205. Further, the whole incubator 200 is covered by a light shield cover 208. Rotation of the incubator 200 is driven by a belt mechanism, which is not illustrated, and the incubator 200 is driven in such a manner to rotate clockwise and anticlockwise.

Further, an opening window 203a for light measurement is formed at a center of the bottom of each element chamber 203 on the rotation member 201. The reflection optical density of the dry analysis element 101 is measured through this opening window 203a by the light measurement head 210. A result of measurement by the light measurement head 210 is output to the correction unit 30, illustrated in FIG. 1.

In the present embodiment, measurement is performed by using the dry analysis element of colorimetric type. However, the type of the dry analysis element is not limited to this type. Measurement may be performed by using a potentiometric method using a dry analysis element of electrolytic type.

As illustrated in FIG. 7, the centrifugal separation unit 10 includes a casing 12 that has an open/close lid 10a for protecting a user from rotation of the container 3 for centrifugal separation and forms a storage space 10b for storing the container 3 for centrifugal separation and a rotation table 13 that is provided in the storage space 10b, and on which the container 3 for centrifugal separation is mounted. Further, a lock mechanism (not illustrated) for locking the open/close lid 10a is provided to prevent the open/close lid 10b from opening during rotation of the container 3 for centrifugal separation. Further, an opening 10c for inserting and taking out the nozzle chip 301 is formed on the open/close lid 10a at a position over the container 3 for centrifugal separation. When a user sets the container 3 for centrifugal separation, the open/close lid 10a is opened. When a sample component after centrifugal separation is taken out from the container 3 for centrifugal separation, the nozzle chip 301 is inserted to the opening 10c in a state in which the open/close lid 10a is closed.

The container 3 for centrifugal separation is stored in the storage space 10b in a state in which the open-close lid 10a is open, and mounted on the rotation table 13. The rotation table 13 is rotationally supported by a rotation mechanism (for example, a motor or the like), which is not illustrated. The rotation table 13 rotates the container 3 for centrifugal separation in a state in which center axis C of the container 3 for centrifugal separation mounted on the rotation table 13 and the rotation axis of the rotation table coincide with each other.

Further, a temperature sensor 14 that measures an ambient temperature, a humidity sensor 15 that measures an ambient humidity, and an atmospheric pressure sensor 16 that measures an atmospheric pressure are provided in the vicinity of the rotation table 13 in the storage space 10b of the container 3 for centrifugal separation. Ambient temperature information, ambient humidity information and atmospheric pressure information measured by these sensors are obtained by the ambient temperature information obtainment unit 42, the ambient humidity information obtainment unit 43 and the atmospheric pressure information obtainment unit 41 of the aforementioned information obtainment unit 40, respectively.

Next, the whole operation of the biochemical analysis apparatus 1 of the present embodiment will be described. Here, an operation at the correction unit 30 of the biochemical analysis apparatus 1 will be mainly described.

First, the container 3 for centrifugal separation in which a sample has been stored is set on the rotation table 13 of the centrifugal separation unit 10, and centrifugal separation is performed. In the present embodiment, blood is stored in the container 3 for centrifugal separation, and a blood plasma component is obtained by performing centrifugal separation on the blood.

Next, the dry analysis element 101 is taken out from the element cartridge 13 by the element conveyance mechanism 400, and conveyed to the spot application unit 100.

Then, the spot application nozzle 302 to which the nozzle chip 301 has been attached moves to an upper direction of the container 3 for centrifugal separation. The spot application nozzle 302 moves down, and sucks a blood plasma component in the container 3 for centrifugal separation into the nozzle chip 301. Then, the spot application nozzle 302 moves to the spot application unit 100, and applies a spot of blood plasma component to the dry analysis element 101. Here, it is assumed that the open/close lid 10a of the centrifugal separation unit 10 is open at this time.

Then, the dry analysis element 101 to which a spot of blood plasma component has been applied is inserted to the element chamber 203 in the incubator 200. Next, the element chamber 203 is revolved, and after the dry analysis element 101 is kept at a constant temperature for a predetermined time, the inserted dry analysis element 101 is moved to the position of the measurement head 210, and measurement of a reflection optical density is performed on the dry analysis element 101.

A result of measurement by the light measurement head 210 is output to the correction unit 30. The correction unit 30 calculates, based on the input result of measurement, the concentration of predetermined biochemical substance contained in the blood plasma component.

Meanwhile, as described already, when so-called rotation-type centrifugal separation is performed, a change of air at a gas-liquid interface is fast, and the area of the surface of blood in contact with air is large, compared with a case in which so-called revolution-type centrifugal separation is performed. Therefore, evaporation of a liquid component during centrifugal separation progresses fast, compared with natural evaporation. Especially, when the amount of a liquid component is small, the area of a surface of the liquid component in contact with air is large relative to the volume of the liquid component. Therefore, a change in concentration by evaporation tends to be large.

Figure 9:
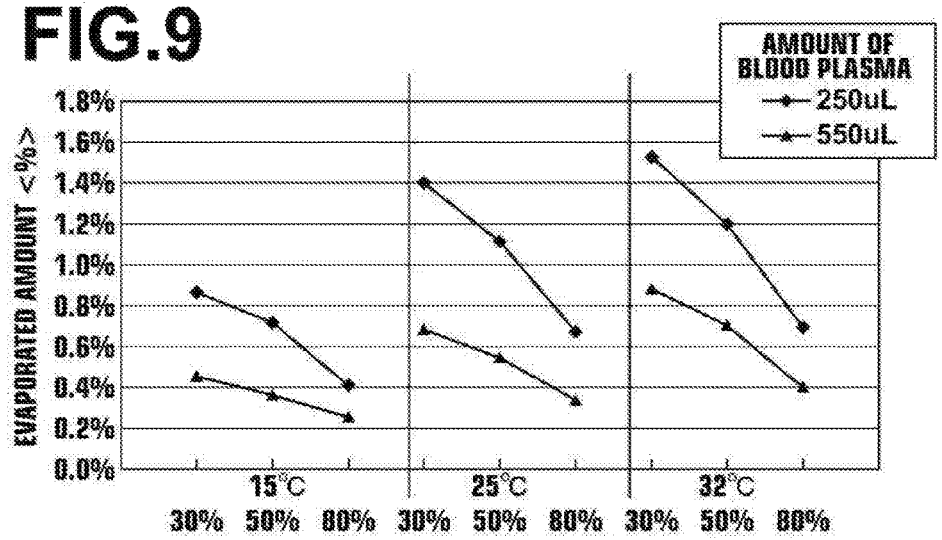
FIG. 9 is a chart showing a result of measuring evaporation amounts of blood plasma components by rotation-type centrifugal separation through experiments.

FIG. 9 shows a result of measuring, through experiments, evaporation amounts of blood plasma components by rotation-type centrifugal separation. FIG. 9 shows relationships of ambient temperature, ambient humidity and the amount of blood plasma component with the evaporation amount. A left graph of FIG. 9 shows evaporation amounts when the ambient temperature was 15° C., and the ambient humidity was changed to 30%, 50% and 80%. A center graph of FIG. 9 shows evaporation amounts when the ambient temperature was 25° C., and the ambient humidity was changed to 30%, 50% and 80%. A right graph of FIG. 9 shows evaporation amounts when the ambient temperature was 32° C., and the ambient humidity was changed to 30%, 50% and 80%. Further, measurement was performed for a case in which the amount of blood plasma component was 250 μL, and a case in which the amount of blood plasma component was 550 μL. As the condition of centrifugal separation, rotation was performed at a rotation speed of 18000 $min^{-1}$ for 120 seconds.

As the graph of FIG. 9 shows, the evaporation amount increased as the ambient temperature was higher. The evaporation amount decreased as the ambient humidity was higher, and the evaporation amount was larger as the amount of blood plasma component was smaller.

Therefore, the correction unit 30 of the present embodiment performs correction operation processing on the result actually measured by the measurement unit 20. The correction operation processing is performed to correct a change in the concentration of biochemical substance caused by evaporation of blood plasma component as described above.

Specifically, as correction operation processing, the correction unit 30 of the present embodiment calculates evaporation amount J (%) based on the following expression (1), and calculates concentration C2 of biochemical substance in which a change in concentration by evaporation has been corrected based on concentration C1 of the biochemical substance that has been actually measured and the following expression (2):

$$\text{Evaporation Amount } J\ (\%) = \{A \times V \times T \times R + B \times T \times R + C \times V \times R + D \times V \times T + E \times R + F \times T + G \times V + H\} \times (t \pm 120) \times (101 \pm P) \quad (1),$$

where V is the amount (μL) of a blood plasma component, T is ambient temperature (° C.), R is ambient humidity (%), t is the length of time (s) of centrifugal separation, and P is atmospheric pressure (kPa). These kinds of information have been obtained by the information obtainment unit 40. Further, in the above expression (1), A through H are constants obtained based on the results of experiments, as shown in the following table 1.

TABLE 1

| | |
|---|---|
| A | 3.500E−09 |
| B | −5.616E−06 |
| C | 1.290E−07 |
| D | −5.586E−07 |
| E | −4.879E−05 |
| F | 6.726E−04 |
| G | −1.274E−05 |
| H | 6.667E−03 |

$$\text{Concentration } C2 \text{ after Correction} = \text{Concentration } C1 \text{ before Correction} \times (1 - \text{Evaporation amount } J\ (\%)/100) \quad (2).$$

For example, when evaporation amount J calculated by the above expression (1) is 1.5%, and concentration C1, which has been actually measured, is 10 mg/dL, concentration C2 after correction is 9.85 mg/dL.

Then, the correction unit 30 outputs concentration C2, on which correction operation processing has been performed, to the output unit 50. The output unit 50 displays received concentration C2, on which correction operation has been performed, on a display device, or outputs concentration C2 to a data server apparatus and stores, or outputs concentration C2 to a printing device and outputs it as a printed sheet.

Figure 10:
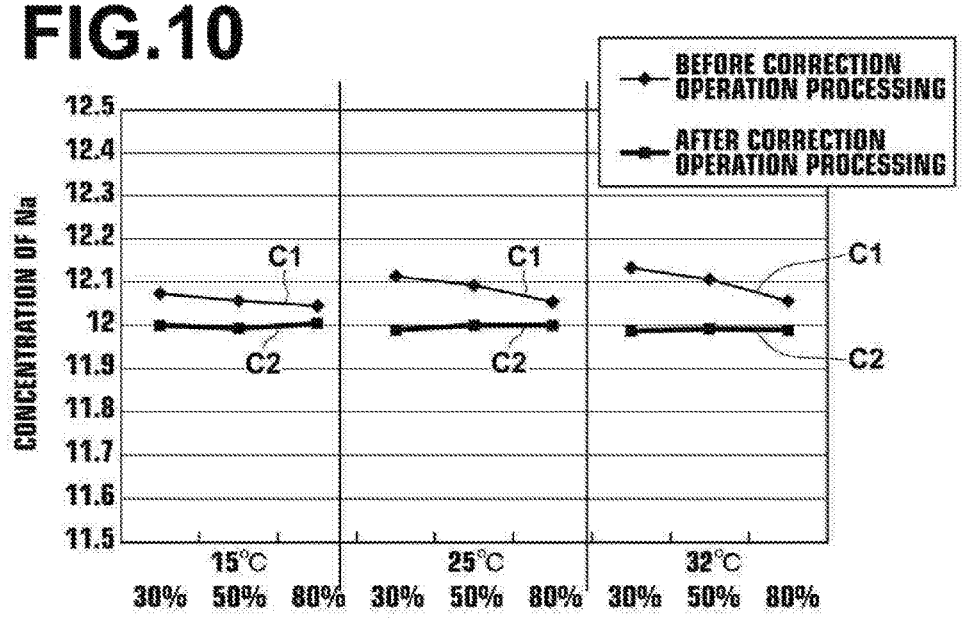
FIG. 10 is a chart showing a result of comparing concentration C2 on which correction operation processing has been performed and concentration C1 before the correction operation processing.

Next, the effect of the aforementioned correction operation processing of the present embodiment will be described. FIG. 10 shows a result of comparing concentration C2 on which correction operation processing of the present embodiment has been performed and concentration C1 before the correction operation processing. Actual concentration C1 before correction operation processing shown in FIG. 10 is the concentration of whole blood of a man (male) of 45 years of age. Centrifugal separation was performed on 1 mL of whole blood with a hematocrit value of 40% for two minutes by rotation-type centrifugal separation, and a blood plasma component was obtained. FIG. 10 shows a result of measuring the concentration of Na in the blood plasma component. FIG. 10 shows the result of measuring the concentration of Na when the ambient temperature was 15° C., 25° C. and 32° C., and the humidity was changed to 30%, 50% and 80%. At this time, atmospheric pressure was 101 kPa. As the measurement unit, FDC7000 (manufactured by FUJIFILM Corporation) was used. As the dry analysis element, a dry analysis element of electrolytic type was used. Further, concentration C2 after actual correction operation processing shown in FIG. 10 is a result obtained by performing correction operation processing on concentration C1, which was actually measured under the aforementioned conditions, by using the above expression (1) and the above expression (2).

Meanwhile, centrifugal separation was performed on the aforementioned whole blood by using ACNO-3 (manufactured by Atom vet's medical), which is a revolution-type centrifugal separation apparatus, and a blood plasma component was obtained. The concentration of Na in the obtained blood plasma component was 12 mmol/L. Here, this value is regarded as a true value.

According to the graph shown in FIG. 10, it was found that concentration C2 after correction operation processing is closer to 12 mmol/L, which is the true value, compared with concentration C1 before correction operation processing. In other words, it was found that a change in concentration caused by evaporation of the blood plasma component in concentration C2 after correction operation processing was less.

In the aforementioned embodiment, evaporation amount J was calculated by substituting actual information about ambient temperature, ambient humidity, atmospheric pressure, the length of time of centrifugal separation and the amount of blood plasma component in the above expression (1). However, it is not always necessary that actual values are obtained for all of these kinds of information. A fixed value or values may be used for a part of these kinds of information. For example, FIG. 11 shows concentration C2 after correction operation processing when actual values were substituted only for ambient temperature, ambient humidity and the length of time of centrifugal separation, and fixed values were used for atmospheric pressure and the amount of blood plasma component. Here, atmospheric pressure was 101 kPa, and the amount of blood plasma component was 400 μL. When concentration C1 was actually measured, the amount of blood plasma component was 250 μL. As the graph of FIG. 11 shows, a value close to 12 mmol/L, which is the true value, was obtainable also when fixed values were used as the amount of blood plasma component and the value of atmospheric pressure and concentration C2 was calculated by using the above expression (1) and the above expression (2).

Further, FIG. 12 shows concentration C2 after correction operation processing when actual values were substituted only for the amount of blood plasma component, ambient humidity and the length of time of centrifugal separation, and fixed values were used for ambient temperature and atmospheric pressure. Here, atmospheric pressure was 101 kPa, and ambient temperature was 25° C. When concentration C1 was actually measured, the amount of blood plasma component was 400 μL. As the graph of FIG. 12 shows, a value close to 12 mmol/L, which is the true value, was obtainable also when fixed values were used as the ambient temperature and the value of atmospheric pressure and concentration C2 was calculated by using the above expression (1) and the above expression (2).

Further, FIG. 13 shows concentration C2 after correction operation processing when actual values were substituted only for the amount of blood plasma component, ambient temperature and the length of time of centrifugal separation, and fixed values were used for ambient humidity and atmospheric pressure. Here, atmospheric pressure was 101 kPa, and ambient humidity was 50%. When concentration C1 was actually measured, the amount of blood plasma component was 400 μL. As the graph of FIG. 13 shows, a value close to 12 mmol/L, which is the true value, was obtainable also when fixed values were used as the ambient humidity and the value of atmospheric pressure and concentration C2 was calculated by using the above expression (1) and the above expression (2).

Further, FIG. 14 shows concentration C2 after correction operation processing when actual values were substituted only for ambient humidity and the length of time of centrifugal separation, and fixed values were used for the amount of blood plasma component, ambient temperature and atmospheric pressure. Here, the amount of blood plasma component was 400 μL, atmospheric pressure was 101 kPa and ambient temperature was 25° C. When concentration C1 was actually measured, the amount of blood plasma component was 250 μL. As the graph of FIG. 14 shows, a value close to 12 mmol/L, which is the true value, was obtainable also when fixed values were used as the amount of blood plasma component, the ambient temperature and the value of atmospheric pressure and concentration C2 was calculated by using the above expression (1) and the above expression (2).

The results of correction operation processing in FIG. 11 through FIG. 14 show that when evaporation amounts are calculated by using the above expression (1), it is not always necessary to use actual values for all of ambient temperature, ambient humidity and the amount of blood plasma component, and that a fixed value or values may be used as a part of these values.

Figure 15:
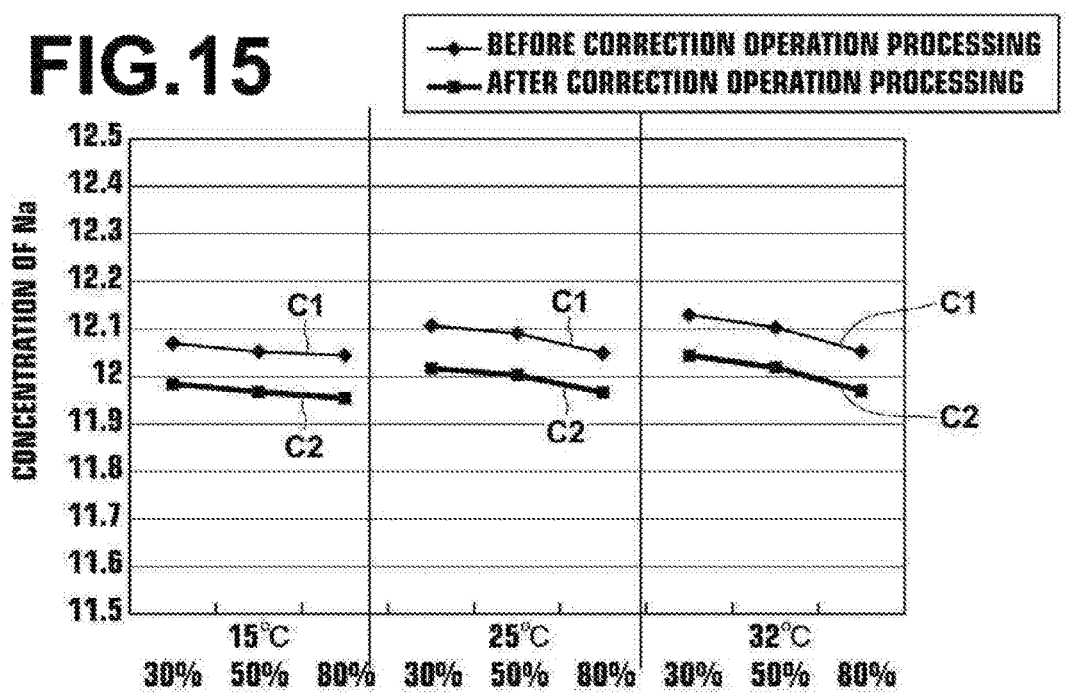
FIG. 15 is a chart showing concentration C2 after correction operation processing when a fixed value of 0.7% is used as an evaporation amount.

In the above embodiment, evaporation amount J was calculated by using the above expression (1). Alternatively, evaporation amount J may be a fixed value. FIG. 15 shows a graph when concentration C2 was calculated by using the above expression (2) while a fixed value of 0.7% was used as evaporation amount J. As the graph of FIG. 15 shows, a value close to 12 mmol/L, which is the true value, was obtainable also when concentration C2 was calculated by using the above expression (2) while a fixed value was used as evaporation amount J.

In the above embodiment, as shown in the above expression (2), an increase in the concentration of Na by evaporation of the blood plasma component was subtracted from the actually measured concentration. However, for example, when a target to be measured is $TCO_2$ contained in blood plasma component, a part of $TCO_2$ is also discharged together with the blood plasma component by evaporation of the blood plasma component.

Therefore, when the target to be measured is $TCO_2$, the amount of discharged $TCO_2$ may be added to the actual measurement result by performing correction operation processing by using the following expression (3) instead of the above expression (2):

Concentration C2 after Correction=Concentration C1 before Correction×(1+3×Evaporation amount J (%))     (3).

In the above expression (3), the numerical value "3" by which the evaporation amount is multiplied is a numerical value that has been obtained in advance based on a result of experiments.

However, the numerical value by which the evaporation amount is multiplied may be changed, for example, based on the kind of a target to be measured. Specifically, for example, a correspondence table between the kinds of plural targets to be measured and numerical values by which the evaporation amount is multiplied may be stored in advance in the apparatus. Further, the numerical value by which the evaporation amount is multiplied may be set by receiving an input by a user about the kind of a target to be measured or by receiving information about the kind of the target to be measured based on a dot code given to a reagent, as in the case of FDC7000 (manufactured by FUJIFILM Corporation), and by referring to the table.

Further, an operation expression for correction operation processing, such as the above expression (2) and the above expression (3), may be modified based on the kind of a target to be measured, such as the concentration of Na and $TCO_2$. Specifically, for example, the kinds of plural targets to be measured and operation expressions used in correction operation processing may be correlated to each other, and stored in the apparatus. Further, an input by a user about the kind of a target to be measured or information about the kind of the target to be measured based on a dot code given to a reagent, as in the case of FDC7000 (manufactured by FUJIFILM Corporation), may be received, and an operation expression used in correction operation processing corresponding to the kind of the target to be measured may be set.

Further, as described above, the measurement unit 20 in the biochemical analysis apparatus 1 of the present embodiment is able to measure not only a biochemical substance contained in a sample that has been centrifugally separated by the centrifugal separation unit 10 built in the biochemical analysis apparatus 1 but also a biochemical substance contained in a sample that has been centrifugally separated by an external centrifugal separation unit 2. When measurement is performed on a sample component that has been centrifugally separated by the external centrifugal separation apparatus 2, the correction unit 30 may skip the aforementioned correction operation processing. In this case, the output unit 50 may display a result of actual measurement on a display device, or output the result to a printing device.

Alternatively, when measurement is performed on the sample component that has been centrifugally separated by the external centrifugal separation apparatus 2, the correction unit 30 may set zero to constants A through H (hereinafter, referred to as operation parameters) in the above expression (1), instead of skipping the correction operation processing. Meanwhile, information as to whether a sample component that has been centrifugally separated by the built-in centrifugal separation unit 10 is measured or a sample component that has been centrifugally separated by the external centrifugal separation unit 2 is measured should be input by a user by using the input unit 60.

Further, it is not always necessary that zero are set to the operation parameters. For example, operation parameters corresponding to the external centrifugal separation apparatus 2 may be set in advance, and operation processing of the above expression (1) may be performed by using the operation parameters. Further, a correspondence table between the kinds of plural external centrifugal separation apparatuses and operation parameters may be stored in advance in the apparatus. Further, operation parameters may be set by receiving an input by a user about the kind of an external centrifugal separation apparatus, and by referring to the table. Here, the operation parameters corresponding the kinds of the external centrifugal separation apparatuses should be obtained in advance by experiments or the like.

In the aforementioned expression (1), evaporation amount J is calculated by taking the amount of blood plasma component into consideration. This amount of blood plasma component may be set by an input by a user using the input unit 60. Alternatively, the amount of blood plasma component may be measured, for example, by using a sensor or the like.

When a user sets the amount of blood plasma component by an input using the input unit 60, it is not always necessary that the user directly inputs the amount of blood plasma component. For example, a user may set, by an input, a hematocrit value and the amount of whole blood dispensed in a container for centrifugal separation, and the correction unit 30 may calculate the amount of blood plasma component by using the following expression (4):

$$\text{The Amount of Blood Plasma Component} = \text{The Amount of Whole Blood} \times (1 - \text{Hematocrit Value} (\%)/100) \quad (4).$$

Further, when the amount of blood plasma component is calculated based on the above expression (4), the amount of whole blood may be measured by using a sensor or the like, instead of being set by an input by the user. Alternatively, the amount of blood plasma component after centrifugal separation may be directly measured by using a sensor or the like.

Figure 16:
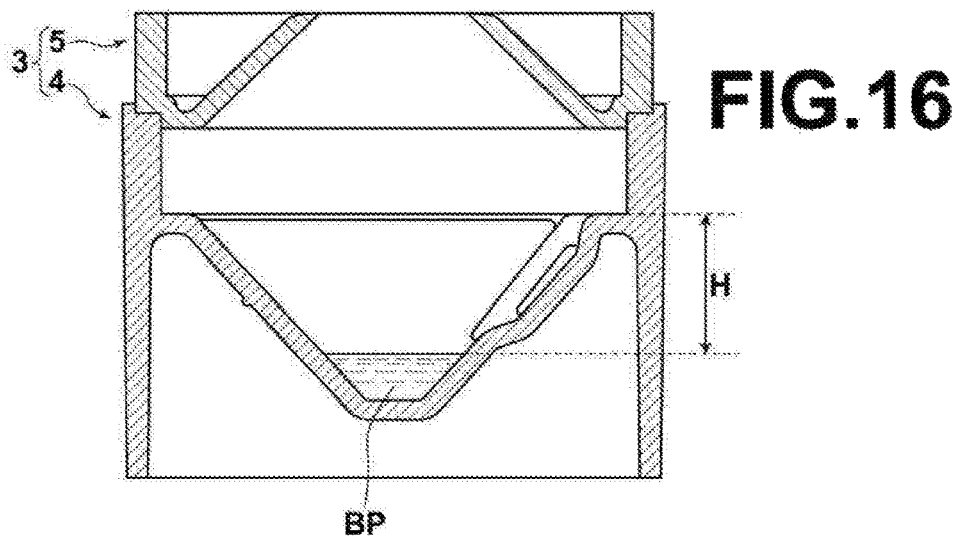
FIG. 16 is a diagram for explaining a method for measuring the amount of a blood plasma component or the like by using a liquid surface detection sensor.
Figure 17:
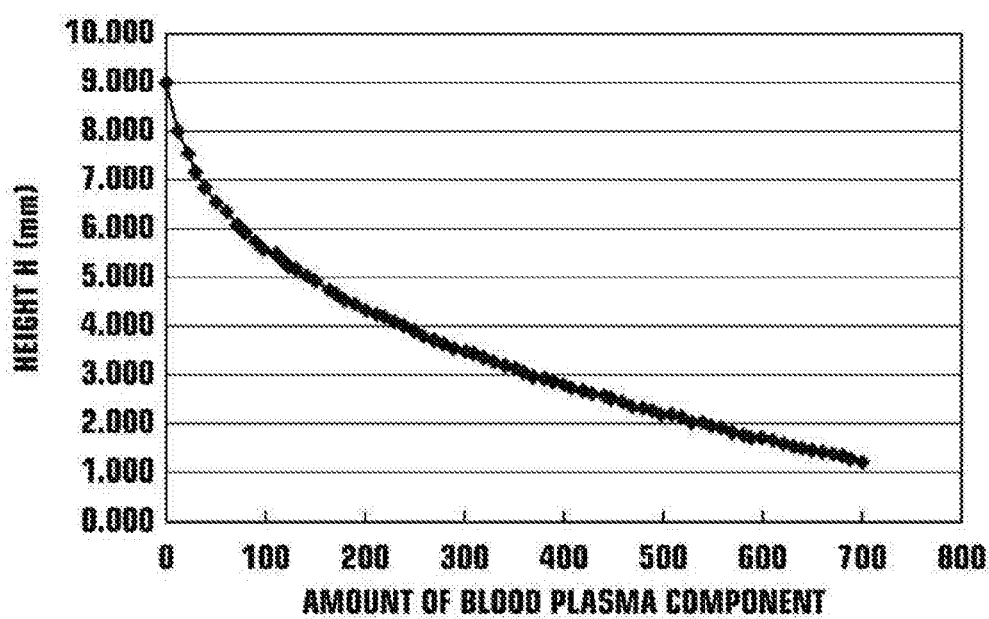
FIG. 17 is a table showing a relationship between height H of the liquid surface of a blood plasma component stored in a container for centrifugal separation and the amount of the blood plasma component.

As a method for measuring the amount of blood plasma component and the amount of whole blood by a sensor, a weight sensor may be used. Alternatively, a liquid surface of the blood plasma component or the whole blood may be detected by using a liquid surface detection sensor, and the amount may be calculated based on the height of this liquid surface. Specifically, as illustrated in FIG. 16, height H of the liquid surface of whole blood or blood plasma component stored in the container 3 for centrifugal separation may be measured, and the amount of whole blood or the amount of blood plasma component may be calculated based on this height H. With respect to a relationship between height H of a liquid surface and the amount of whole blood or blood plasma component, a table, for example as shown in FIG. 17, should be set in advance. Further, various known sensors may be used, as the liquid surface detection sensor.

Here, when the amount of blood plasma component is measured by a sensor as described above, it is desirable that the amount of blood plasma component is measured each time when a biochemical substance in a blood plasma component is measured, and that correction operation processing is performed by using the amount obtained by measurement.

Figure 18:
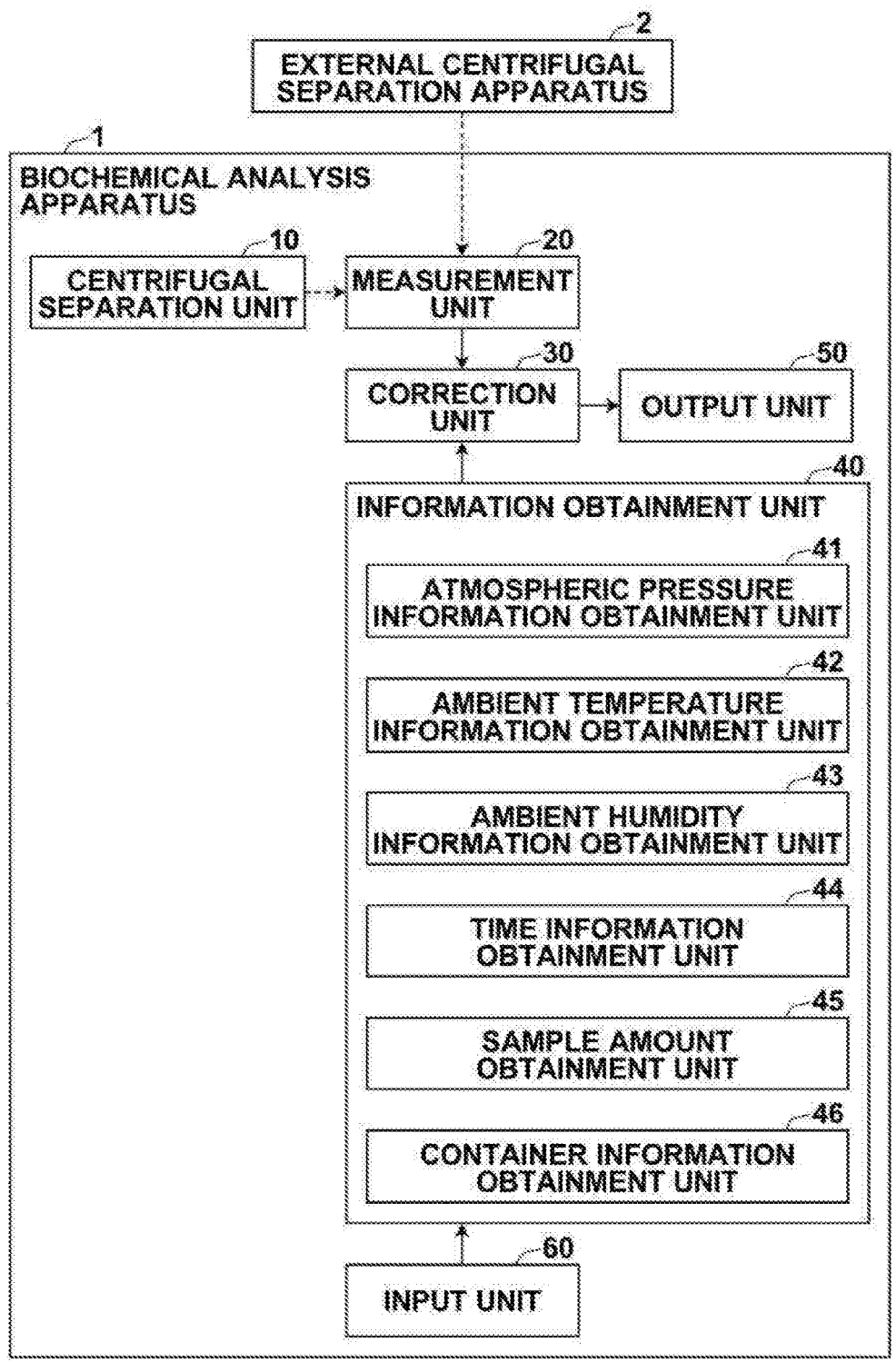
FIG. 18 is a schematic block diagram illustrating the configuration of a biochemical analysis apparatus using another embodiment of a measurement apparatus of the present disclosure.
Figure 19:
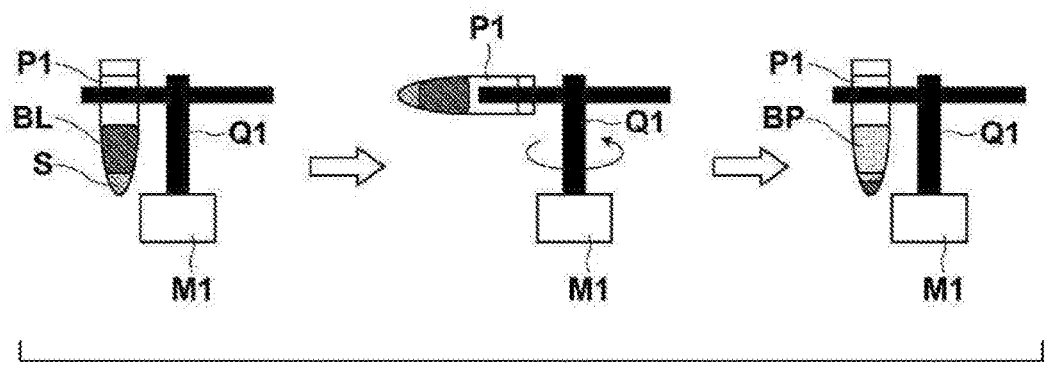
FIG. 19 is a schematic diagram illustrating the configuration of a revolution-type centrifugal separation apparatus and its operation.
Figure 20:
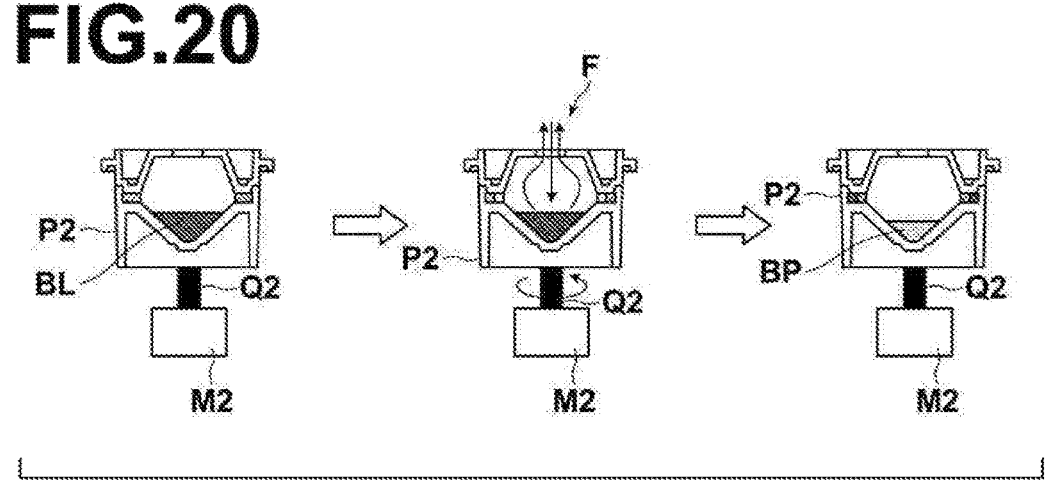
FIG. 20 is a schematic diagram illustrating the configuration of a rotation-type centrifugal separation apparatus and its operation.

Further, in the aforementioned embodiment, when plural containers for centrifugal separation in different size (volume) are used, the area of a surface of a sample in a container for centrifugal separation in contact with air differs according to the size of the container. Therefore, the evaporation amount of the sample by centrifugal separation also differs. Therefore, as illustrated in FIG. 18, a container information obtainment unit 46 may be further provided, and the operation parameters in the above expression (1) may be set based on information about the kind of a container for centrifugal separation obtained by this container information obtainment unit 46. Specifically, for example, operation parameters corresponding to plural kinds of containers for centrifugal separation should be stored in the correction unit 30 in advance, and operation parameters should be set based on the information about the container for centrifugal separation that has been obtained by the container information obtainment unit 46.

The information about the kind of the container for centrifugal separation may be set by an input by a user using the input unit 60. Alternatively, an IC (Integrated Circuit) tag or barcode or the like in which information about the kind of the container is stored may be set on each container for centrifugal separation, and these kinds of information may be obtained by the user by reading them by using a reader device or the like connected to the apparatus. Alternatively, the information about the kind of the container may be obtained by automatically reading out the information in the apparatus. Further, as the information about the kind of the container for centrifugal separation, the capacity or the diameter of the opening of the container or the like may be used.

What is claimed is:

1. A measurement apparatus comprising:
    a centrifugal separation unit that performs centrifugal separation on a sample that has been injected into a container by rotating the container about a center axis of the container, as a rotation axis;
    a measurement unit that measures a sample component in the container that has been centrifugally separated by the centrifugal separation unit;
    a correction unit that performs, on a result of the measurement, correction operation processing based on a change in concentration caused by evaporation of the sample during the centrifugal separation; and
    an atmospheric pressure information obtainment unit that obtains atmospheric pressure information,
    wherein the correction unit performs, based on the atmospheric pressure information, the correction operation processing on the result of measurement.

2. The measurement apparatus, as defined in claim 1,
    wherein the measurement unit measures also a sample component that has been centrifugally separated by an external centrifugal separation unit other than the centrifugal separation unit, and
    wherein the correction unit does not perform the correction operation processing on a result of the measurement of the sample component that has been centrifugally separated by the external centrifugal separation unit or performs the correction operation processing on the result of the measurement of the sample component that has been centrifugally separated by the external centrifugal separation unit by using an operation parameter different from an operation parameter that was used when the correction operation processing was performed on the result of measurement of the sample component that had been centrifugally separated by the centrifugal separation unit.

3. The measurement apparatus, as defined in claim 1, the apparatus further comprising:
   a temperature information obtainment unit that obtains ambient temperature information,
   wherein the correction unit performs, based on the ambient temperature information, the correction operation processing on the result of measurement.

4. The measurement apparatus, as defined in claim 1, the apparatus further comprising:
   a humidity information obtainment unit that obtains ambient humidity information,
   wherein the correction unit performs, based on the ambient humidity information, the correction operation processing on the result of measurement.

5. The measurement apparatus, as defined in claim 1, the apparatus further comprising:
   a time information obtainment unit that obtains information about the length of time of the centrifugal separation,
   wherein the correction unit performs, based on the information about the length of time of the centrifugal separation, the correction operation processing on the result of measurement.

6. The measurement apparatus, as defined in claim 1, the apparatus further comprising:
   a sample amount information obtainment unit that obtains information about the amount of the sample component that has been centrifugally separated,
   wherein the correction unit performs, based on the information about the amount of the sample component, the correction operation processing on the result of measurement.

7. The measurement apparatus, as defined in claim 6, wherein when the sample is blood, the sample amount information obtainment unit obtains information about a hematocrit value of the blood, and obtains, based on the information about the hematocrit value, information about the amount of a blood plasma component, as the information about the amount of the sample component.

8. The measurement apparatus, as defined in claim 1, the apparatus further comprising:
   an information obtainment unit that obtains atmospheric pressure information, ambient temperature information, ambient humidity information, information about the length of time of the centrifugal separation, and information about the amount of the sample component,
   wherein the correction unit performs, based on the atmospheric pressure information, the ambient temperature information, the ambient humidity information, the information about the length of time of the centrifugal separation, and the information about the amount of the sample component, correction operation processing on the result of the measurement.

9. The measurement apparatus, as defined in claim 1, wherein the measurement unit measures a gas component included in the sample on which the centrifugal separation has been performed, and
   wherein the correction unit performs, based on the amount of the gas component evaporated by the centrifugal separation, the correction operation processing on the result of measurement.

10. The measurement apparatus, as defined in claim 1, the apparatus further comprising:
    a container information obtainment unit that obtains information about a container into which the sample to be measured has been injected,
    wherein the correction unit performs, based on the information about the container, the correction operation processing on the result of measurement.

11. The measurement apparatus, as defined in claim 10, wherein the correction unit stores operation parameters of the correction operation processing that correspond to information about a plurality of containers including the container.

* * * * *